United States Patent [19]

Reed et al.

[11] Patent Number: 5,210,344

[45] Date of Patent: May 11, 1993

[54] DEHYDROHALOGENATION OF 1,1,2-TRICHLOROETHANE USING CYCLIC AMINES

[75] Inventors: Daniel J. Reed; Tarver G. Snedecor, both of Angleton, Tex.

[73] Assignee: The Dow Chemical Company, Midland, Mich.

[21] Appl. No.: 889,531

[22] Filed: May 27, 1992

[51] Int. Cl.$^5$ ............................................. C07C 17/34
[52] U.S. Cl. .................................................... 570/228
[58] Field of Search ......................................... 570/228

[56] References Cited

U.S. PATENT DOCUMENTS

| 2,361,072 | 10/1944 | Vining. |
|---|---|---|
| 2,541,724 | 2/1951 | Stowe et al.. |
| 2,879,311 | 3/1959 | Hawkins. |
| 2,989,570 | 6/1961 | Conrad et al.. |
| 4,230,681 | 10/1980 | Coenen et al.. |

Primary Examiner—Howard T. Mars

[57] ABSTRACT

In a process for production of vinylidene chloride by dehydrohalogenation of 1,1,2-trichloroethane using a base, improved selectively for formation of vinylidene chloride is obtained by using as the base a cyclic amine having a $pK_a$ greater than about 11 as dehydrohalogenating agent.

14 Claims, No Drawings

DEHYDROHALOGENATION OF 1,1,2-TRICHLOROETHANE USING CYCLIC AMINES

BACKGROUND OF THE INVENTION

This invention relates to the production of vinylidene chloride, specifically to dehydrohalogenation of 1,1,2-trichloroethane to produce vinylidene chloride.

Vinylidene chloride is commonly produced by dehydrohalogenation of 1,1,2- trichloroethane using inorganic bases such as calcium hydroxide or sodium hydroxide. The reaction, however, produces large quantities of a corresponding salt, e.g. calcium chloride or sodium chloride.

Thermal and catalytic cracking of 1,1,2-trichloroethane in also known to produce vinylidene chloride. These processes, however, produce undesirable quantities of by-products.

Use of certain amines, quaternary ammonium chloride salts of amines and hydrochloric acid salts of amines having a basic dissociation constant ($pK_b$) less than 7 in the dehydrohalogenation of 1,1,2-trichloroethane is disclosed in U.S. Pat. No. 2,989,570. The process is said to exhibit selectivity for vinylidene chloride over by-products, but conversion of 1,1,2-trichloroethane has been found to be low.

It would be desirable to have a process having selectivity for vinylidene chloride, but in which there is a high conversion of 1,1,2-trichloroethane without production of salt.

SUMMARY OF THE INVENTION

In one aspect, the invention is an improvement in the process for production of vinylidene chloride by dehydrohalogenation of 1,1,2-trichlorethane using a base, the improvement comprising using as the base a cyclic amine having a $pK_a$ greater than about 11 as dehydrohalogenating agent.

In another aspect the invention is a process for the production of vinylidene chloride by dehyrochlorination of 1,1,2-trichloroethane comprising contacting 1,1,2-trichloroethane and a cyclic amine having a $pK_a$ greater than about 11 at a temperature and for a time sufficient for the production of vinylidene chloride.

This reaction has high yields of vinylidene chloride and has a high percentage of vinylidene chloride in the product.

DETAILED DESCRIPTION OF THE INVENTION

This invention involves use of a cyclic amine having a $pK_a$ greater than about 11 as a dehydrochlorinating agent for 1,1,2- trichloroethane. The term cyclic amine is used to mean a heterocyclic compound having at least one basic amine nitrogen in the ring thereof. Such compounds include piperidines, 1,8-diazabicyclo-[5.4.0]-undec-7-ene, (DBU), alkylated derivatives of such heterocyclic compounds.

The $pK_a$ of compounds useful in the practice of the invention is greater than about 11, preferably (for the purpose of achieving higher conversions of starting material to vinylidene chloride) greater than about 11.1, more preferably greater than about 11.2, most preferably equal to or greater than about 11.25. The $pK_a$ is measured by means within the skill in the art such as the methods described in The Determination of Ionization Constants: A Laboratory Manual, A. Albert and E. P. Serjeant, Chupman and Hall, N.Y., 1984. Use of cyclic amines of $pK_a$ lower than about 11 result in relatively lower selectivity to vinylidene chloride. For instance, N-ethyl piperidine with a $pK_a$ of 10.45 results in a product which is about 92.5 percent vinylidene chloride (92.5 percent selectivity).

In most instances, cyclic amines having a $pK_a$ greater than 11 have at least one sterically hindered amine nitrogen. Such compounds are preferred for use in the practice of the invention. More preferably, the compounds have at least one, preferably from one to about 4 lower alkyl groups on the amine nitrogen atom(s) and/or on atoms, preferably carbon atoms, adjacent to an amine group in a heterocyclic ring. Most preferably there are from about 1 to about 3 groups on those atoms. The lower alkyl groups preferably have from 1 to about 6, preferably from 1 to about 4, most preferably from 1 to about 2 carbon atoms.

Most preferably, the compounds have a lower alkyl group on amine nitrogen atom(s), particularly on ring amine nitrogen atom(s). The lower alkyl groups preferably have from 1 to about 6, preferably from 1 to about 3, most preferably from 1 to about 2 carbon atoms. These groups are preferably on carbon atoms which are adjacent nitrogen atoms.

The ring(s) and substituents thereon of the cyclic amines of the invention are unsubstituted or inertly substituted, that is substituted with substituents which do no interfere undesirably with the substituents include alkyl groups of from $C_1$ to $C_{10}$ on compounds having a $pK_a$ greater than about 11.

Exemplary cyclic amines having a $pK_a$ greater than about 11 include 2,2,6,6-tetramethylpiperidine, 1,2,2,6,6-pentamethylpiperidine, 1,8-diazabicyclo-[5.4.0]-undec-7-ene (DBU), 1,5-diazabicyclo [4.3.0]non-5-ene (DBN) and 2,2,4,-trimethylpiperidine.

Preferred cyclic amines among those of a given $pK_a$ are those having a boiling point greater than about 50° C., preferably from about 50° C. to about 250° C. to facilitate removal of the product. For a desirable combination of boiling point and $pK_a$, the preferred compounds are 1,2,2,6,6-pentamethylpiperidine, DBU, DBN, and 2,2,6,6-tetramethylpiperidine, most preferably 1,2,2,6,6-pentamethylpiperidine.

The 1,1,2-trichloroethane and cyclic amine having a $pK_a$ greater than about 11 are contacted at a temperature and for a time sufficient for the production of vinylidene chloride. Any time and temperation combination which results in production of product is suitable for use in the practice of the invention, but temperatures are preferably from about 40° to about 200° C., more preferably from about 80° to about 130° C., with pressures of preferably aobut atmospheric to 100 psig (pounds per square inch gauge), more preferably from about atmospheric to about 50 psig. Contact times are preferably from about 1 minute to about 2 hours, more preferably from about 5 minutes to about 1 hour, most preferably from about 10 minutes to about 30 minutes.

The cyclic amine and 1,1,2-trichloroethane are preferably contacted in a mole ratio of from about 1:40 to about 40:1 preferably about 1:5 to 5:1.

It is preferred that the reactants be contacted in equipment which allows the reactants to be in contact, preferably with mixing, and which allows removal of vinylidene chloride from the reaction. More preferably the vinylidene chloride is continuously removed is continuous, such that 1,1,2-trichloroethane and cyclic amine are fed to the reactor while the amine hydrochloride and vinylidene chloride are concurrently removed. Separation is advantageously accomplished by maintaining the temperature such that vinylidene chloride is continuously removed from a reactor as vinylidene chloride gas boiling from the reaction mixture overhead, and the amine HCl salt and unreacted 1,1,2-trichloromethane are removed from the bottom.

When reactants are contacted as described, the yield of vinylidene chloride based on starting 1,1,2-trichloroethane is very high, preferably greater than about 90 percent, more preferably greater than about 94 percent, most preferably greater than about 98 percent. Additionally, the reaction is preferentially selective for production of vinylidene chloride rather than by-products such as cis- and trans-dichloroethene or monochloroacetylene. Preferably, more than about 94 percent, more preferably more than about 96 percent, most preferably more than about 98 percent by weight of the product(s) produced from 1,1,2-trichloroethane is vinylidene chloride.

The following examples are given to illustrate the invention, but are not to be interpreted as limiting it. Examples of the invention (Ex.) are designated numerically, while comparative samples (C.S.) are designated alphabetically. All ratios, parts and percentages are by weight unless designated otherwise.

EXAMPLES

Example 1: Reaction of DBU ($pK_a = >11.2$) with 1,1,2-trichloroethane in a 1:4.08 mole ratio A reaction vessel equipped with a magnetic stirring bar, Vigreaux column, condenser, and collection flask is charged with 0.6522 moles of 1,1,2-trichloroethane. The reaction vessel is warmed to 45° C., then 0.1598 moles of DBU is added dropwise over 75 minutes (min) and allowed to react for an additional 100 min. The temperature of the reaction vessel increases to 120° C. during a 175 minute reaction time and vinylidene chloride is observed to distill out of the reaction mixture. Both the distillate and reaction flask contents are analyzed by gas chromatography. The yield is 0.1571 moles of vinylidene chloride, 0.0017 moles of cis-1,2-dichloroethene, and 0.493 moles of unreacted 1,1,2-trichloroethane. This corresponds to 100 percent DBU conversion and 98.68 percent selectivity for vinylidene chloride.

This sample shows high vinylidene chloride selectivity using bases with $pK_a$'s of greater than 11.

Example 2: Reaction of 1,2,2,6,6-pentamethylpiperidine (PMP) ($pK_a = 11.25$) with 1,1,2-trichloroethane in a 1:1.7 mole ratio A reaction vessel equipped with a magnetic stirring bar, Vigreaux column, condenser, and collection flask is charged with 0.1777 moles of 1,1,2-trichloroethane and 0.1048 moles of PMP. The temperature of the reaction vessel if increased to 102° C. during a 165 minute reaction time, and vinylidene chloride is observed to distill out of the reaction mixture. Both the distillate and reaction flask contents are analyzed as in Example 1. Analysis shown 0.1020 moles of vinylidene chloride, 0.0031 moles of trans-1,2-dichloroethene, 0.0026 moles of cis-1,2-dichloroethene, and 0.0713 moles of unreacted 1,1,2-trichloroethane. This corresponds to 100 percent PMP conversion and 95.86 percent selectively to vinylidene chloride.

This example shows high vinylidene chloride selectivity using bases with $pK_a$ greater than 11.

Example 3: Reaction of 2,2,6,6-tetramethylpiperidine (TMP) ($pK_a = 11.07$) with 1,1,2-trichloroethane in a 1:1.04 mole ratio A reaction vessel equipped with a magnetic stirring bar, Vigreaux column, condenser, and collection flask is charged with 0.3439 moles of 1,1,2-trichloroethane and 0.3296 moles of TMP. The temperature of the reaction vessel is increased to 103° C. during a 165 minute reaction time, and vinylidene chloride observed to distill out of the reaction mixture. Both the distillate and reaction flask contents are analyzed as in Example 1. Analysis shows 0.0434 moles of vinylidene chloride, 0.0011 moles of trans01,2-dichloroethane, 0.0007 moles of cis-1,2-dichloroethene, and 0.2979 moles of unreacted 1,1,2-trichloroethane. This corresponds to 13.7 percent TMP conversion and 94.34 percent selectivity to vinylidene chloride.

This example shows advantageous selectivity for vinylidene chloride obtained by using a cyclic amine base with a $pK_a$ greater than 11.

By way of comparison it is noted that when an amine having a $pK_a$ less than about 11 is used, selectivity is less than about 92 mole percent.

Comparative Sample A: Reaction of N-ethylpiperidine (NEP) ($pK_a = 10.45$) with 1,1,2-trichloroethane in a 1:1.7 mole ratio A reaction vessel equipped with a magnetic stirring bar, Vigreaux column, condenser, and collection flask is charged with 0.4301 moles of 1,1,2-trichloroethane and 0.2544 moles of NEP. The temperature of the reaction vessel is increased to 110° C. during a 75 minute reaction time, and vinylidene chloride is observed to distill out of the reaction mixture. Both distillate and reaction flask contents are analyzed as in Example 1. Analysis shows 0.1424 moles of vinylidene chloride, 0.0071 moles of trans-1,2-dichloroethane, 0.0045 moles of cis-1,2-dichloroethene, and 0.2744 moles of unreacted 1,1,2-trichloroethane. This corresponds to 61.20 percent NEP conversion and 91.45 percent selectivity to vinylidene chloride.

The comparative sample shows selectivity for vinylidene chloride is less when a compound with less than a $pK_a$ of 11 is used as base is lower than when a base with $pK_a$ greater than 11 is used.

Comparative Sample B: Reaction of 2,4,5-trimethylpyridine (TMPy), $pK_a 32$ 7.43 with 1,1,2-trichloroethane in a 4.85:1 mole ratio A reaction vessel equipped with a magnetic stirring bar, Vigreaux column, condenser, and collection flask are charged with 0.1094 moles of 1,1,2-trichloroethane and 0.5311 moles of TMPy. The temperature of the reaction vessel is increased to 110° C. during a 270 minute reaction time, and vinylidene chloride is observed to distill out of the reaction mixture. Both the distillate and reaction flask contents are analyzed as in Example 1. Analysis shows 0.0032 moles of vinylidene chloride, 0.0006 moles of trans-1,2-dichloroethene, 0.0003 moles of cis-1,2-dichloroethene, and 0.1053 moles of unreacted 1,1,2-trichloroethane. This corresponds to 0.77 percent TMPy conversion and 78.04 percent selectivity to vinylidene chloride.

This comparative sample shows selectivity for vinylidene chloride is lower when a base with a $pK_a$ less than 11.0 is used that when a base of $pK_a$ greater than 11 is used.

What is claimed is:

1. In a process for dehydrohalogenation of 1,1,2-tirchloroethane to produce vinylidene chloride, an improvement comprising using a cyclic amine having a $pK_a$ greater than about 11 as dehydrohalogenating agent.

2. The process of claim 1 wherein the cyclic amine is a piperidine.

3. The process of claim 2 wherein the piperidine is alkyl substituted on the amine nitrogen or on at least one carbon atom adjacent or a nitrogen atom with at least one alkyl group having from 1 to about 6 carbon atoms.

4. The process of claim 3 wherein there are from about 1 to about 3 alkyl groups.

5. The process of claim 4 wherein each alkyl group has from 1 to about 4 carbon atoms.

6. The process of claim 1 wherein the cyclic amine is an 1,8-diazabicyclo-5,4,0-undec-7-ene.

7. The process of claim 6 wherein the 1,8-diazabicyclo-[5,4,0-undec-7-ene is alkyl substituted on the amine nitrogen or on at least carbon atom adjacent to a nitrogen atom with at least one alkyl group having from 1 to about 6 carbon atoms.

8. The process of claim 7 wherein there are from 1 to about 3 alkyl groups.

9. The process of claim 8 wherein each alkyl group has from 1 to about 4 carbon atoms.

10. The process of claim 1 wherein the $pK_a$ is greater than about 11.2.

11. The process of claim 1 wherein the $pK_a$ is greater than about 11.25.

12. The process of claim 1 wherein the cyclic amine is selected from 2,2,6,6-tetramethylpiperidine, 1,2,2,6,6-pentamethylpiperidine, 1,8-diazabicyclo-[5.4.0]-undec-7-ene (DBU), 1,5-diazabicyclo [4.3.0]non-5-ene (DBN) and 2,2,4,-trimethylpiperidine.

13. The process of claim 12 wherein the cyclic amine is selected from 1,2,2,6,6-pentamethylpiperidine, DBU, DBN, and 2,2,6,6-tetramethylpiperidine.

14. The process of claim 13 wherein the cyclic amine is 1,2,2,6,6-pentamethylpiperidine.

* * * * *